US012201452B2

(12) United States Patent
Patolsky et al.

(10) Patent No.: US 12,201,452 B2
(45) Date of Patent: Jan. 21, 2025

(54) METHOD AND SYSTEM FOR SUBCUTANEOUS SENSING

(71) Applicant: Ramot at Tel-Aviv University Ltd., Tel-Aviv (IL)

(72) Inventors: Fernando Patolsky, Rehovot (IL); Vadim Krivitsky, Bney-Ayish (IL); Omri Heifler, Tzukey Yam (IL); Marina Zverzhinetsky, Rishon-LeZion (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 16/326,385

(22) PCT Filed: Aug. 22, 2017

(86) PCT No.: PCT/IL2017/050935
§ 371 (c)(1),
(2) Date: Feb. 19, 2019

(87) PCT Pub. No.: WO2018/037407
PCT Pub. Date: Mar. 1, 2018

(65) Prior Publication Data

US 2019/0223795 A1 Jul. 25, 2019

Related U.S. Application Data

(60) Provisional application No. 62/377,775, filed on Aug. 22, 2016.

(51) Int. Cl.
*A61B 5/00* (2006.01)
*A61B 5/145* (2006.01)
(Continued)

(52) U.S. Cl.
CPC .......... *A61B 5/685* (2013.01); *A61B 5/14514* (2013.01); *A61B 5/14532* (2013.01);
(Continued)

(58) Field of Classification Search
CPC .................. A61B 5/1495; A61B 5/685; A61B 2562/0285; A61B 5/4839; A61B 5/14532;
(Continued)

(56) References Cited

U.S. PATENT DOCUMENTS

| | | | |
|---|---|---|---|
| 7,619,290 | B2 | 11/2009 | Lieber et al. |
| 2002/0082543 | A1 | 6/2002 | Park et al. |

(Continued)

FOREIGN PATENT DOCUMENTS

| | | |
|---|---|---|
| CN | 106164286 | 11/2016 |
| KR | 2011-0124855 | 11/2011 |

(Continued)

OTHER PUBLICATIONS

Supplementary European Search Report and the European Search Opinion Dated Feb. 27, 2020 From the European Patent Office Re. Application No. 17843058.3. (7 Pages).

(Continued)

*Primary Examiner* — Benjamin S Melhus
*Assistant Examiner* — Severo Antonio P Lopez

(57) ABSTRACT

A system for monitoring at least presence of a bioanalyte. The system comprises: a substrate having a skin contact surface, a microneedle outwardly protruding from the skin contact surface, a sensing complex positioned in the microneedle, and a circuit attached to the substrate. The sensing complex can comprise a nanostructure modified by a functional moiety covalently attached thereto, and an affinity moiety effective to react specifically with the bioanalyte to produce a reaction product. The circuit can apply voltage to the nanostructure and monitor changes in an (Continued)

electrical property of the nanostructure responsively to reaction between the reaction product and the functional moiety.

11 Claims, 4 Drawing Sheets

(51) Int. Cl.
*A61B 5/1473* (2006.01)
*A61B 5/1486* (2006.01)
*A61B 5/1495* (2006.01)
*A61M 37/00* (2006.01)

(52) U.S. Cl.
CPC ...... *A61B 5/14735* (2013.01); *A61B 5/14865* (2013.01); *A61B 5/1495* (2013.01); *A61B 5/4839* (2013.01); *A61B 5/6833* (2013.01); *A61M 37/0015* (2013.01); *A61B 2562/0285* (2013.01); *A61M 2037/0023* (2013.01); *A61M 2037/003* (2013.01); *A61M 2037/0061* (2013.01)

(58) Field of Classification Search
CPC ...... A61M 37/0015; A61M 2037/0061; A61M 2037/0023
See application file for complete search history.

(56) References Cited

U.S. PATENT DOCUMENTS

| | | | | |
|---|---|---|---|---|
| 2002/0117659 | A1 | 8/2002 | Lieber et al. | |
| 2002/0133129 | A1 | 9/2002 | Arias et al. | |
| 2003/0153900 | A1* | 8/2003 | Aceti | A61B 5/150076 604/890.1 |
| 2003/0190632 | A1 | 10/2003 | Sosnlwski et al. | |
| 2007/0111196 | A1* | 5/2007 | Alarcon | A61L 2/208 435/4 |
| 2009/0170209 | A1 | 7/2009 | Machauf et al. | |
| 2010/0022012 | A1 | 1/2010 | Lieber et al. | |
| 2010/0152057 | A1 | 6/2010 | Lieber et al. | |
| 2010/0325073 | A1 | 12/2010 | Haick | |
| 2012/0134880 | A1 | 5/2012 | Kurkina et al. | |
| 2012/0172692 | A1 | 7/2012 | Tamada et al. | |
| 2012/0187000 | A1 | 7/2012 | Kahn et al. | |
| 2012/0265034 | A1* | 10/2012 | Wisniewski | A61B 5/14532 600/309 |
| 2014/0286875 | A1* | 9/2014 | Gamsey | A61K 49/0073 424/9.61 |
| 2015/0231633 | A1 | 8/2015 | Dubin et al. | |
| 2015/0307936 | A1 | 10/2015 | Goldsmith | |
| 2015/0376692 | A1 | 12/2015 | Esfandyarpour et al. | |
| 2016/0095541 | A1 | 4/2016 | Wang et al. | |
| 2019/0227028 | A1 | 7/2019 | Patolsky et al. | |

FOREIGN PATENT DOCUMENTS

| | | |
|---|---|---|
| KR | 101359349 | 1/2014 |
| WO | WO 2010/099446 | 9/2010 |
| WO | WO 2011/000443 | 1/2011 |
| WO | WO 2012/137207 | 10/2012 |
| WO | WO 2015/059704 | 4/2015 |
| WO | WO 2015/192064 | 12/2015 |
| WO | WO 2016/032335 | 3/2016 |
| WO | WO 2018/037406 | 3/2018 |
| WO | WO 2018/037407 | 3/2018 |

OTHER PUBLICATIONS

Supplementary European Search Report and the European Search Opinion Dated Feb. 10, 2020 From the European Patent Office Re. Application No. 17843059.1. (8 Pages).

Katz et al. "Glucose Oxidase Electrodes via Reconstitution of the Apo-Enzyme: Cailoring of Novel Glucose Biosensors", Analytica Chimica Acta, XP8043785, 385,(1-3): 45-58, Apr. 5, 1999.

International Preliminary Report on Patentability Dated Mar. 7, 2019 From the International Bureau of WIPO Re. Application No. PCT/IL2017/050933. (7 Pages).

International Preliminary Report on Patentability Dated Mar. 7, 2019 From the International Bureau of WIPO Re. Application No. PCT/IL2017/050935. (7 Pages).

International Search Report and the Written Opinion Dated Dec. 4, 2017 From the International Searching Authority Re. Application No. PCT/IL2017/050933. (25 Pages).

International Search Report and the Written Opinion Dated Dec. 10, 2017 From the International Searching Authority Re. Application No. PCT/IL2017/050935. (12 Pages).

Chen et al. "Silicon Nanowire Field-Effect Transistor-Based Biosensors for Biomedical Diagnosis and Cellular Recording Investigation", Nano Today, 6(2): 131-154, Available Online Mar. 8, 2011.

Clavaguera et al. "Sub-PPM Detection of Nerve Agents Using Chemically Functionalized Silicon Nanoribbon Field-Effect Transistors", Angewandte Chemie International Edition, 49(24): 4063-4066, Jun. 1, 2010.

Cui et al. "Nanowire Nanosensors for Highly Sensitive and Selective Detection of Biological and Chemical Species", Science, 293(5533): 1289-1292, Aug. 17, 2001.

Duan et al. "Intracellular Recordings of Action Potentials by an Extracellular Nanoscale Field-Effect Transistor", Nature Nanotechnology, 7(3): 174-179, Published Online Dec. 18, 2011.

Griffin et al. "Metabolic Profiles of Cancer Cells", Nature Reviews Cancer, 4(7): 551-561, Jul. 2004.

Han et al. "Mutiscale Substrates Based on Hydrogel-Incorporated Silicon Nanowires for Protein Patterning and Microarray-Based Immunoassays", Biosensors and Bioelectronics, 45: 129-135, Available Online Feb. 6, 2013.

Kosaka et al. "Detection of Cancer Biomarkers in Serum Using a Hybrid Mechanical and Optoplasmonic Nanosensor", Nature Nanotechnology, 9(12): 1047-1053, Published Online Nov. 2, 2014.

Krivitsky et al. "Si Nanowires Forest-Based On-Chip Biomolecular Filtering, Separation and Preconcentration Devices: Nanowires Do It All", Nano Letters, 12(9): 4748-4756, Published Online Aug. 2, 2012.

Li et al. "Sequence-Specific Label-Free DNA Sensors Based on Silicon Nanowires", Nano Letters, 4(2): 245-247, Feb. 11, 2004.

Lu et al. "A Nano-Ni Based Ultrasensitive Nonenzymatic Electrochemical Sensor for Glucose: Enhancing Sensitivity Through a Nanowire Array Strategy", Biosensors and Bioelectronics, 25(1): 218-223, Published Online Jul. 7, 2009.

Lu et al. "Enzyme-Functionalized Gold Nanowires for the Fabrication of Biosensors", Bioelectrochemistry, 71(2): 211-216, Published Online Jun. 14, 2007.

Munoz-Pinedo et al. "Cancer Metabolism: Current Perspectives and Future Directions", Cell Death and Disease, 3(1): e248-1-e248-10, Jan. 12, 2012.

Patolsky et al. "Electrical Detection of Single Viruses", Proc. Natl. Acad. Sci. USA, PNAS, 101(39): 14017-14022, Sep. 28, 2004.

Patolsky et al. "Nanowire-Based Biosensors", Analytical Chemistry, 78(13): 4260-4269, Jul. 1, 2006.

Piao et al. "Enzyme Incorporated Microfluidic Device for In-Situ Glucose Detection in Water-in-Air Microdroplets", Biosensors and Bioelectronics, 65: 220-225, Available Online Oct. 18, 2014.

Revzin et al. "Fabrication of Poly(Ethylene Glycol) Hydrogel Microstructures Using Photolithography", Langmuir, 17(18): 5440-5447, Published Jul. 18, 2001.

Shao et al. "Silicon Nanowire Sensors for Bioanalytical Applications: Glucose and Hydrogen Peroxide Detection", Advanced Functional Materials, 15(9): 1478-1482, Sep. 1, 2005.

Stern et al. "Label-Free Biomarker Detection From Whole Blood", Nature Nanotechnology, 5(2): 138-142, Published Online Dec. 13, 2009.

Stern et al. "Semiconducting Nanowire Field-Effect Transistor Biomolecular Sensors", IEEE Transactions on Electron Devices, 55(11): 3119-3130, Nov. 2008.

Su et al. "A Silicon Nanowire-Based Electrochemical Sensor With High Sensitivity and Electrocatalytic Activity", Particle Particle Systems Characterization, 30(4): 326-331, Apr. 1, 2013.

(56) References Cited

OTHER PUBLICATIONS

Timko et al. "Electrical Recording From Hearts With Flexible Nanowire Device Arrays", Nano Letters, 9(2): 914-918, Feb. 2009.
Tyagi et al. "Patternable Nanowire Sensors for Electrochemical Recording of Dopamine", Analytical Chemistry, 81(24): 9979-9984, Dec. 15, 2009.
Yang et al. "Gold Nanoparticle Modified Silicon Nanowires as Biosensors", Nanotechnology, 17(11): S276-S279, May 19, 2006.
Zheng et al. "Multiplexed Electrical Detection of Cancer Markers With Nanowire Sensor Arrays", Nature Biotechnology, 23(10): 1294-1301, Oct. 2005.
Notification of Office Action and Search Report Dated May 8, 2021 From the State Intellectual Property Office of the People's Republic of China Re. Application No. 201580052710.1 (13 Pages).
Translation Dated Jun. 10, 2021 of Notification of Office Action and Search Report Dated May 8, 2021 From the State Intellectual Property Office of the People's Republic of China Re. Application No. 201580052710.1 (19 Pages).
Aulicino et al. "Temporal Perturbation of the Wnt Signaling Pathway in the Control of Cell Reprogramming Is Modulated by TCF1", Stem Cell Reports 2(5):707-720, May 6, 2014.
Gafni et al. "Derivation of Novel Human Ground State Naive Pluripotent Stem Cells", Nature 504:282-286, Oct. 30, 2013.
Murayama et al. "Successful Reprogramming of Epiblast Stem Cells by Blocking t, Juclear Localization of ß-Catenin", Stem Cell Reports 4(1):103-113, Jan. 13, 2015.
Notification of Office Action and Search Report Dated Aug. 10, 2021 From the State Intellectual Property Office of the People's Republic of China Re. Application No. 201780064812.4. (16 Pages).
Official Action Dated Jun. 10, 2022 from US Patent and Trademark Office Re. U.S. Appl. No. 16/326,960. (14 pages).
Cao et al. "Ionophore-Containing Siloprene Membranes: Direct Comparison between Conventional Ion-Selective Electrodes and Silicon Nanowire-Based Field-Effect Transistors", Analytical Chemistry, 87(2): 1173-1179, Dec. 9, 2014.
Reinhoudt et al. "The Transduction of Host-Guest Interactions into Electronic Signals by Molecular Systems", Advanced materials, 2(1): 23-32, Jan. 1990.
Official Action Dated Feb. 23, 2022 from US Patent and Trademark Office Re. U.S. Appl. No. 16/326,960. (19 pages).
Lee et al. "Periodic Array of Polyelectrolyte-Gated Organic Transistors from Electrospun Poly (3-hexylthiophene) Nanofibers", Nano Letter, 10(1): 347-351, 2010.
Sharma et al. "Graphene and Graphene Oxide Materials for Chemo- and Biosensing of Chemical and Biochemical Hazards", Making and Exploiting Fullerenes, Graphene, and Carbon Nanotubes, 348: 237-265, 2013.
Communication Pursuant to Article 94(3) EPC Dated Sep. 29, 2022 From the European Patent Office Re. Application No. 17843058.3. (5 Pages).
Official Action Dated Oct. 6, 2022 from US Patent and Trademark Office Re. U.S. Appl. No. 16/326,960. (17 pages).
Munoz et al. "Photosensitive Polyurethanes Applied to the Development of CHEMFET and ENFET Devices for Biomedical Sensing", Biosensors and Bioelectronics, 12(7): 577-585, 1997.
Advisory Action Dated Jan. 18, 2023 from the US Patent and Trademark Office Re. U.S. Appl. No. 16/326,960. (4 pages).
Official Action Dated Mar. 8, 2023 from the US Patent and Trademark Office Re. U.S. Appl. No. 16/326,960. (14 pages).
Buenger et al. "Hydrogels in Sensing Applications", Progress in Polymer Science, 37(12): 1678-1719, Dec. 2012.

* cited by examiner

METHOD AND SYSTEM FOR SUBCUTANEOUS SENSING

RELATED APPLICATION

PCT Patent Application No. PCT/IL2017/050935 was co-filed on Aug. 22, 2017 with PCT Patent Application No. PCT/IL2017/050933, titled "METHODS AND SYSTEMS FOR DETECTING BIOANALYTES", which claims the benefit of priority of U.S. Provisional Patent Application No. 62/377,776 filed on Aug. 22, 2016, the contents of which are incorporated herein by reference in their entirety.

This application is a National Phase of PCT Patent Application No. PCT/IL2017/050935 having International filing date of Aug. 22, 2017, which claims the benefit of priority of U.S. Provisional Patent Application No. 62/377,775 filed on Aug. 22, 2016. The contents of the above applications are all incorporated herein by reference in their entirety.

FIELD AND BACKGROUND OF THE INVENTION

The present invention, in some embodiments thereof, relates to sensing and, more particularly, but not exclusively, to a system and a method for subcutaneous sensing of, for example, metabolic activity.

Metabolism is defined as the totality of biochemical processes in living organisms that either produce or consume energy. Metabolic processes regulate cells to grow or die, reform their structures, and respond to their environments. Abnormal metabolic reactions disturb normal physiology and lead to severe tissue dysfunction, and are linked to many diseases.

Diabetes mellitus is a widely distributed disease caused by either the failure of the pancreas to produce insulin or the body's inability to use insulin. Patients diagnosed with diabetes mellitus may suffer blindness, loss of extremities, heart failure and many other complications over time. In is recognized that there is no "cure" for the disease, but rather only treatment, most commonly with insulin injections in order to change the blood-glucose level.

To maintain a normal lifestyle, the diabetic patient must carefully and continuously monitor his or her blood glucose level on a daily, and oftentimes hourly basis. For example, blood glucose levels are critical in the maintenance and determination of cognitive functioning. With respect to the brain, blood glucose levels with respect to the brain influence and affect memory, awareness and attention. The consequences of reduced or elevated blood glucose levels on cognitive function are therefore more severe for subjects with poor glucose control such as individuals afflicted with diabetes. Hyperglycemia refers to a condition in which the blood glucose is too high, and the hyperglycemic subject is in danger of falling into coma. Hypoglycemia refers to a condition in which the blood glucose is too low, and the hypoglycemic subject is in danger of developing tissue damage in the blood vessels, eyes, kidneys, nerves, etc.

Foremost in the management of diabetes and the attainment of a successful insulin therapy is the need to continuously monitor the blood glucose level. Historically, this has been accomplished through repetitive blood glucose tests requiring finger pricks three to four times daily. The primary reason for this regimen is that blood glucose levels fluctuate and stay out of balance until the next test or injection, and such fluctuations and imbalances greatly increase the risk of tissue and organ damage. The established method of glucose measurement expresses samples of blood onto a disposable test strip, and utilizes a meter device to read the test strip and report a quantitative blood glucose concentration. The appropriate dose of insulin is then calculated, measured and administered with a hypodermic needle.

U.S. Publication No. 20020082543 discloses a device for transport of molecules or energy across or into a biological barrier. The device includes one or more microneedles, each formed of two materials, wherein the one of the materials is dispersed throughout a portion of the other material or forms a portion of the microneedle.

WO 2012/137207 describes a method of measuring a metabolic activity of a cell, effected by independently measuring in an extracellular environment of the cell, time-dependent acidification profiles due to secretion of non-volatile soluble metabolic products; non-volatile soluble metabolic products and volatile soluble metabolic products; and volatile soluble metabolic products, and uses of such a method for diagnosing and monitoring disease treatment.

WO2015/059704 describes a system having a chamber in controllable fluid communication with a sensing compartment. The chamber contains a fluid and the sensing compartment comprises a semiconductor nanostructure and a functional moiety covalently attached to the nanostructure. The functional moiety is such that upon contacting a redox reactive agent, the nanostructure exhibits a detectable change in an electrical property.

SUMMARY OF THE INVENTION

According to an aspect of some embodiments of the present invention there is provided a system for monitoring at least presence of a bioanalyte. The system comprises: a substrate having a skin contact surface, a microneedle outwardly protruding from the skin contact surface, a sensing complex positioned in the microneedle, and a circuit attached to the substrate. According to some embodiments of the invention the sensing complex comprises a nanostructure modified by a functional moiety covalently attached thereto, and an affinity moiety effective to react specifically with the bioanalyte to produce a reaction product. According to some embodiments of the invention the circuit is configured for applying voltage to the nanostructure and monitoring changes in an electrical property of the nanostructure responsively to reaction between the reaction product and the functional moiety.

According to some embodiments of the invention wherein the nanostructure comprises a semiconductor nanostructure.

According to some embodiments of the invention to some embodiments of the invention the nanostructure comprises a conductive nanostructure. According to some embodiments of the invention the nanostructure comprises a carbon nanotube.

According to some embodiments of the invention the affinity moiety is immobilized to the nanostructure.

According to some embodiments of the invention the affinity moiety is immobilized to a medium in the microneedle, other than the nanostructure.

According to some embodiments of the invention the medium is a hydrogel.

According to some embodiments of the invention the affinity moiety is immobilized to an integral wall of the microneedle.

According to some embodiments of the invention the skin contact surface is adherent to a skin of a subject.

According to some embodiments of the invention the system comprises a drug delivery system having an actuator, attached to or integral with the substrate, and a controller configured to receive a signal pertaining to the binding from the circuit and operate the actuator to deliver a drug via a channel responsively to the signal.

According to some embodiments of the invention the channel is in an additional microneedle, outwardly protruding from the substrate.

According to some embodiments of the invention the sensing complex comprises a transistor, wherein the nanostructure is a charge carrier channel in the transistor. According to some embodiments of the invention the circuit is configured for applying a gate voltage to a gate of the transistor.

According to some embodiments of the invention the reaction product comprises a redox reactive species, wherein the reaction between the reaction product and the functional moiety is a redox reaction, and wherein the circuit is configured for controlling the gate voltage such as to reverse the redox reaction.

According to some embodiments of the invention the system comprises a calibration microneedle, outwardly protruding from the skin contact surface, and having therein a calibration complex which comprises a calibration nanostructure modified by the functional moiety covalently attached thereto, but is devoid of the affinity moiety; wherein the circuit is configured for applying voltage to the calibration nanostructure and subtract changes in an electrical property of the calibration nanostructure from the changes in the electrical property of the nanostructure.

According to an aspect of some embodiments of the present invention there is provided a method of monitoring at least presence of a bioanalyte. The method comprises: introducing into a skin of a subject, a microneedle having therein a sensing complex comprises a nanostructure modified by a functional moiety covalently attached thereto, and an affinity moiety effective to react specifically with the bioanalyte to produce a reaction product; applying voltage to the nanostructure; and monitoring changes in an electrical property of the nanostructure responsively to reaction between the reaction product and the functional moiety.

According to some embodiments of the invention the introducing comprises establishing contact between the skin and a skin contact surface of a substrate, wherein the microneedle outwardly protrudes from the skin contact surface.

According to some embodiments of the invention the method comprises delivering a drug through the skin via a channel responsively to the monitoring. According to some embodiments of the invention the channel is in the microneedle. According to some embodiments of the invention the channel is in an additional microneedle, and the method comprises introducing also the additional microneedle.

According to some embodiments of the invention the sensing complex comprises a transistor, wherein the nanostructure is a charge carrier channel in the transistor.

According to some embodiments of the invention the method comprises applying gate voltage to a gate of the transistor.

According to some embodiments of the invention the reaction product comprises a redox reactive species, wherein the reaction between the reaction product and the functional moiety is a redox reaction, and wherein the method comprises controlling the gate voltage such as to reverse the redox reaction.

According to some embodiments of the invention the method comprises: introducing into a skin of a subject a calibration microneedle, outwardly protruding from the skin contact surface, and having therein a calibration complex which comprises a calibration nanostructure modified by the functional moiety covalently attached thereto, but is devoid of the affinity moiety; applying voltage to the calibration nanostructure; and subtracting changes in an electrical property of the calibration nanostructure from the changes in the electrical property of the nanostructure. According to some embodiments of the invention the calibration complex comprises a non-sensing moiety. According to some embodiments of the invention the functional moiety is a redox reactive moiety.

According to some embodiments of the invention the functional moiety comprises at least one functional group capable of reversible change in an oxidation number or oxidation state of at least one of its atoms.

According to some embodiments of the invention the functional moiety comprises a quinone. According to some embodiments of the invention the functional moiety comprises an aromatic quinone.

According to some embodiments of the invention the functional moiety is or comprises a functional group elected from the group consisting of quinone, benzoquinone, anhraquinone, and phenanthrenequinone, each being substituted or unsubstituted.

According to some embodiments of the invention the affinity moiety comprises an enzyme.

According to some embodiments of the invention the affinity moiety comprises a redox enzyme.

According to some embodiments of the invention the affinity moiety comprises glucose oxidase.

According to some embodiments of the invention the affinity moiety comprises an immunogenic moiety.

According to some embodiments of the invention the immunogenic moiety comprises an antibody or a fragment thereof.

According to some embodiments of the invention the immunogenic moiety comprises an antigen and wherein the bioanalyte comprises an antibody to the antigen.

According to some embodiments of the invention the affinity moiety comprises a ligand and the bioanalyte comprises a receptor.

According to some embodiments of the invention the affinity moiety is effective to bind specifically with the bioanalyte to produce the reaction product.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
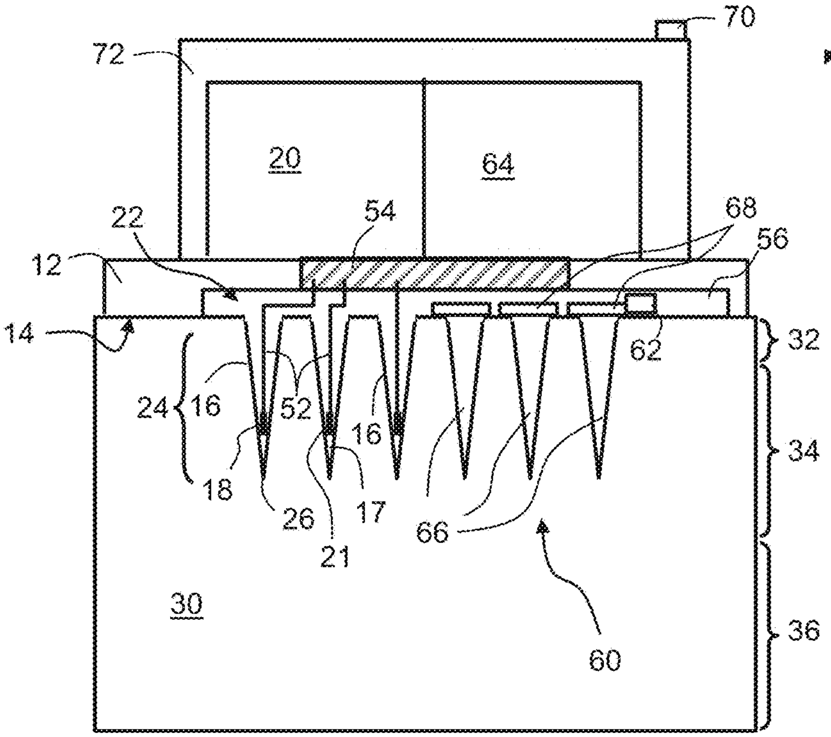
FIGS. 1A-D are schematic illustrations of a system for monitoring presence, absence or level of a bioanalyte according to some embodiments of the present invention.

The present invention, in some embodiments thereof, relates to sensing and, more particularly, but not exclusively, to a system and a method for subcutaneous sensing of, for example, metabolic activity.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventors have devised and successfully prepared and practiced an integrated microfluidic sensing system, comprised of a substrate having a skin contact surface, a microneedle outwardly protruding from the skin contact surface, a sensing complex positioned in the microneedle, and a circuit attached to the substrate. The present inventors have shown that using such a system can be used for real-time monitoring of various bioanalytes in the body of the subject. The system can also comprise a drug delivery system and can therefore be utilized for the administration of a compound to a subject. The administration can be in closed loop control with the monitoring. For example, the system can be used for monitoring glucose levels and for delivering insulin at a controlled rate, to a diabetic subject who would normally need multiple daily injections to regulate the blood glucose level.

Referring now to the drawings, FIGS. 1A-D are schematic illustrations of a system 10 for monitoring presence, absence or level of a bioanalyte according to some embodiments of the present invention. System 10 preferably comprises a substrate 12 having a skin contact surface 14 for contacting a skin 30 of a subject (human or animal), and one or more sensing microneedles 16, outwardly protruding from skin contact surface 14. System 10 also comprises one or more sensing complexes 18 positioned in sensing microneedle(s) 16, and a circuit 20 attached to substrate 12. Optionally, but not necessarily, circuit 20 is at an opposite side of substrate 12 relative to microneedle(s) 16. Any of the microneedles of system 10 can have any shape, including, without limitation, a conical shape, a cylindrical shape, a tubular shape and a pyramidal shaped. A hook-shaped microneedle is also contemplated. The microneedle is preferably straight, but non-straight shapes (e.g., a curved shape microneedle, a hook-shaped microneedle, or semi hook-shaped microneedle) are also contemplated. The microneedle can protrude perpendicularly from surface 14, or at an acute angle from surface 14. The microneedle typically has a base 22, attached to or being integral with substrate 12, and a penetrating portion 24 extending away from base 22. Penetrating portion 24 has a tip 26, optionally and preferably a tapered tip, distal to base 22.

The microneedle is preferably hollow or provided with a microchannel embedded therein, and contains at least one opening for allowing the microneedle to exchange fluids with a medium outside the microneedle.

Figure 1B:
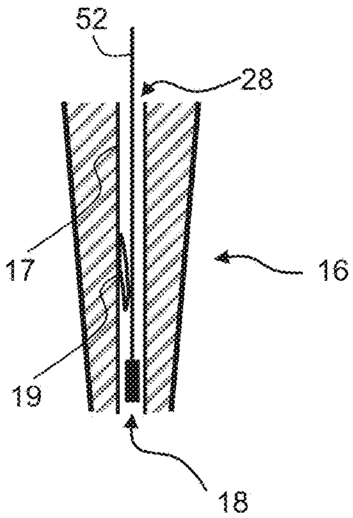

FIG. 1B is a magnified schematic illustration showing a portion of sensing microneedle 16 with a microchannel 28 extending lengthwise through its body.

The term "microchannel" as used herein refers to a fluid channel having cross-sectional dimensions the largest of which being less than 1 mm, more preferably less than 500 μm, more preferably less than 400 μm, more preferably less than 300 μm, more preferably less than 200 μm, e.g., 100 μm or smaller.

Typically, but not necessarily the microneedle has an opening at tip 26. The microneedle 16 or a portion thereof can optionally and preferably be porous.

Alternatively, the microneedle can be non-porous with only one or a few openings formed on its body. The microneedle is preferably made of a non-degradable material. The diameter of base 22 is typically from about 1 μm to about 500 μm. In some embodiments, the diameter of the microneedle is selected to leave a residual hole (following microneedle insertion and withdrawal) of less than about 1 μm, to avoid making a hole which would allow bacteria to enter the penetration wound. The length of penetrating portion 24 is preferably selected to allow penetrating portion 24 to penetrate into skin 30, preferably beyond the stratum corneum layer 32. Preferably, but not necessarily, the length of penetrating portion 24 is selected to positioning tip 26 in the viable epidermis layer 34 but not in the dermis layer 36. A typical length of penetrating portion 24 is from about 0.1 mm to about 0.5 mm, e.g., about 0.3 mm.

The microneedle(s) of system 10 can be constructed from any of a variety of materials, including, without limitation metals, ceramics, semiconductors, organics, polymers, and composites. Preferred materials of construction include pharmaceutical grade stainless steel, gold, titanium, nickel, iron, tin, chromium, copper, palladium, platinum, alloys of these or other metals, silicon, silicon dioxide, and polymers. The microneedle preferably has a mechanical strength to remain intact while being inserted into the skin 30, while remaining in place, and while being removed. The microneedle is preferably sterile. Any sterilization procedure can be employed, including, without limitation, ethylene oxide or gamma irradiation.

A plurality of microneedles used in accordance with some embodiments of the present invention may include a mixture of different microneedles. For example, microneedles of the plurality may include microneedles having various lengths, base portion materials, body portion diameters (i.e., gauge), tip portion shapes, spacing between microneedles, coatings, etc.

Typically, substrate 12 can be provided in the form of a skin patch. Surface 14 is optionally and preferably an adherent surface for allowing substrate 12 to be attached to skin 30. For example, surface 14 can comprise, or be coated with a skin adhesive material. Optionally substrate 12 also contains a substance selected for preventing or reducing skin irritation, such as, but not limited to, pruritus, flush, rash, pain, eczema, skin inflammation. Preferably, substrate 12 is flexible. For example, substrate 12 can be made, at least in part of a woven fabric, a nonwoven fabric, a plastic film or the like. The substrate can be, for example, an elastomeric polymer substrate. Suitable elastomeric polymer substrate materials are generally selected based upon their compatibility with the manufacturing process (soft lithography, stereo lithography and three-dimensional jet printing, etc.). Given the tremendous diversity of polymer chemistries, precursors, synthetic methods, reaction conditions, and potential additives, there is a large number of materials that are contemplated for use as substrate 12. Representative examples of elastomeric polymers include, without limitation, polydimethylsiloxane (PDMS), polyisoprene, polybutadiene, polychloroprene, polyisobutylene, poly(styrene-butadiene-styrene), polyurethanes and silicones. Polymers which are generally non-elastomeric are also contemplated. Representative examples of such polymers include, without limitation, PMMA and polycarbonate.

Also contemplated are embodiments in which the skin patch is made of two or more materials. For example, a portion of the skin patch can be made from a woven or nonwoven fabric, or film, optionally and preferably coated with a skin adhesive material, while another portion serves as a microfluidic interface 56, wherein microneedles 16, are formed on or integral with microfluidic interface 56. Microfluidic interface 56 can be made more rigid than the fabric or film.

The lateral dimensions of substrate may vary, depending on the size of the organ of the subject that receives surface 14. A typical lateral diameter of substrate 12 is, without limitation, from about 10 mm to about 50 mm.

Figure 1C:
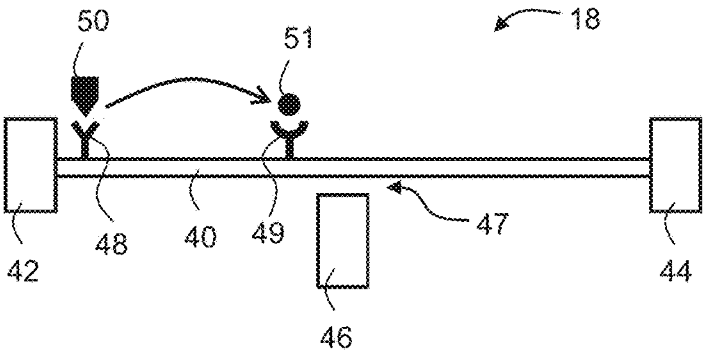

Sensing complex 18 preferably comprises an affinity moiety and a nanostructure modified by a functional moiety. A magnified schematic illustration of sensing complex 18 according to some embodiments of the present invention is shown in FIG. 1C. Shown in FIG. 1C are an affinity moiety 48 and a nanostructure 40 modified by a functional moiety 49. Functional moiety 49 is optionally and preferably covalently attached to nanostructure 40. In the representative illustration of FIG. 1C, which is not to be considered as limiting, affinity moiety 48 is shown immobilized to nanostructure 40. However, this need not necessarily be the same since for some applications, affinity moiety 48 can be not immobilized or immobilized to a medium 19 in microneedle 16 other than nanostructure 40 (e.g., immobilized to a hydrogel) or immobilized to an integral wall 17 of microneedle 16. Affinity moiety 48 is effective to react (e.g., bind) specifically to a bioanalyte 50, to produce to produce a reaction product 51 which in turn reacts with functional moiety 49. In some embodiments, affinity moiety 48 is also referred to herein as "sensing moiety).

In some embodiments, affinity moiety 48 and bioanalyte 50 are members of an affinity pair, wherein moiety 48 is capable of reversibly or non-reversibly binding with high affinity (characterized by a Kd (Dissociation constant) of, e.g., less than $10^{-7}$ M, e.g., less than $10^{-8}$ M, less than $10^{-9}$, less than $10^{-10}$ M) to bioanalyte 50. For example, the affinity pair can be an enzyme-substrate pair, a polypeptide-polypeptide pair (e.g., a hormone and receptor, a ligand and receptor, an antibody and an antigen, two chains of a multimeric protein), a polypeptide-small molecule pair (e.g., avidin or streptavidin with biotin, enzyme-substrate), a polynucleotide and its cognate polynucleotide such as two polynucleotides forming a double strand (e.g., DNA-DNA, DNA-RNA, RNA-DNA), a polypeptide-polynucleotide pair (e.g., a complex formed of a polypeptide and a DNA or RNA e.g., aptamer), a polypeptide-metal pair (e.g., a protein chelator and a metal ion), a polypeptide and a carbohydrate (leptin-carbohydrate), and the like.

According to some embodiments of the invention, moiety 48 is an enzyme, preferably, but not necessarily a redox enzyme. Representative examples of enzymes suitable for the present embodiments include, without limitation, glucose oxidase, beta-galactosidase, alkaline phosphatase, beta-glucoronidase, lactate oxidase, pyruvate oxidase. In preferred embodiments, moiety 48 is glucose oxidase and bioanalyte 50 is glucose.

Functional moiety 49 can be any moiety 49 that is capable of reacting with reaction product 51 and change, optionally and preferably in a reversible manner, one or more of the electrical property of nanostructure 40 as a result of this reaction. Representative examples of functional moieties suitable for use as functional moiety 49 according to some embodiments of the present invention are found in International Patent Application, Publication No. WO2015/059704, the contents of which are hereby incorporated by reference.

The reaction between reaction product 51 and functional moiety 49 can be a redox reaction. In these embodiments reaction product 51 comprises a redox reactive species.

As used herein and in the art, the phrase "redox reactive species" describes a moiety or a compound that can participate in a redox reaction or reduction-oxidation reactions, either as an oxidizer or a reductant, and is capable of altering an oxidation number of one or more atoms of another substance. This phrase is used herein throughout to describe both an oxidizer and a reductant.

Herein throughout, for any one of the embodiments described herein for any of the aspects of the present invention, an "oxidizer", which is also referred to herein interchangeably as "an oxidizing/oxidative agent" or "an oxidizing/oxidative moiety" or "an oxidizing/oxidative species" describes a moiety, species or a compound that is capable of elevating the oxidation number of one or more atoms of another substance. Typically, such an alteration involves transformation of protons from the other substance to the oxidizing moiety or compound.

Exemplary oxidizing agents that are suitable for being detected using a sensing system as described herein include, but are not limited to, reactive oxygen species (ROS) or compounds generated by reactive oxygen species.

As used herein throughout reactive oxygen species include oxygen-containing molecules and/or ions in which an oxygen atom is in a free radical form (having an unpaired electron) or molecules or ions that readily generate species featuring one or oxygen free radical or oxygen in singlet state. Examples include, without limitations: ozone, peroxides, RO., and ROO., in which R is an organic moiety or hydrogen. In the presence of water or any other protic solvent, ROS typically generate hydrogen peroxide. Hydrogen peroxide or any other peroxide is therefore an exemplary oxidizing agent according to some embodiments of the present invention.

Herein throughout, for any one of the embodiments described herein for any of the aspects of the present invention, a "reductant", which is also referred to herein interchangeably as "a reducing/reductive agent" or "a reducing/reductive moiety" or "a reducing/reductive species" describes a moiety, species or a compound that is capable of reducing the oxidation number of another substance. Typically, such an alteration involves transformation of protons from the reducing agent to the other substance.

Suitable reducing agents include, for example, moieties or species that upon release of one or more protons form a stable anion. Exemplary such agents include, for example, hydroxyl-containing agents that form a stable enolate anion upon releasing one or more protons. Compounds or moiety containing an amine-oxide group are given herein as an example. N-alkyl- or N,N-dialkyl-hydroxyl amines (e.g., DMHA) are given as a representative example. Any other known reducing agents are also contemplated.

According to some embodiments of the present invention, functional moiety 49 is a redox-reactive moiety.

Preferably, the functional moiety is such that can easily be transformed from a reduced state to oxidized state, and vice versa, namely, features a change in the oxidation number of its atom(s) at a low energy barrier. The functional moiety can be regarded as such that can feature a reversible change in an oxidation number of one or more of its atoms, namely, a reversible redox change or transformation. A reversible redox change of a moiety or group can be determined, for example, by cyclic voltametry measurements.

Exemplary functional moieties are such that feature a redox potential that ranges from about −1.0 to about 1.0 Volt, or from −0.8 to 0.8 Volt, or from −0.6 to 0.6 Volt or from −0.5 to 0.5 Volt, or from −0.4 to 0.4 Volt, or from −0.3 to 0.3 Volt or from −0.2 to 0.2 Volt, or from −0.1 to 0.1 Volt, as well as lower potentials and any value there between.

Functional moiety 49 can comprise at least one functional group that is capable of undergoing a reversible redox change, as described herein.

In some of any of the embodiments described herein for functional moiety 49, a length of the functional moiety is smaller than 2 nm, smaller than 1.5 nm, and even smaller than 1 nm. This allows the formation of the charge transfer complex to occur close to the nanostructures' surface, thereby enhancing the device's sensitivity.

In some of any of the embodiments described herein, functional moiety 49 is selected such that a Debye length of at least 100 nm, at least 500 nm, at least 800 nm and even 1 micron and higher is exhibited.

As used herein and in the art, the phrase "Debye length" describes the distance over which significant charge separation can occur.

An exemplary functional moiety comprises at least one functional group that is capable of undergoing a keto-enol tautomerization, as this term is well known in the art.

Moieties comprising one or more functional groups capable of undergoing keto-enol redox reaction include, for example, a quinone moiety and can be collectively represented by the following scheme 1:

Scheme 1

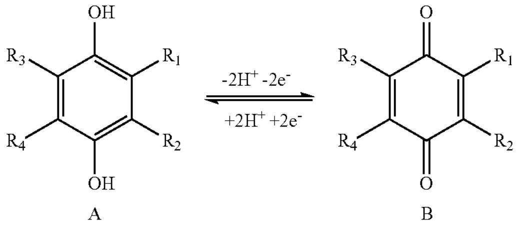

wherein $R_1$-$R_4$ are each independently selected from the group consisting of hydrogen, alkyl, aryl, cycloalkyl, halo, trihaloalkyl, alkoxy, carboxy and any other chemically compatible substituent, as described herein, or, alternatively, $R_1$ and $R_2$ and/or $R_3$ and $R_4$ form together a carbocylic ring, which can be substituted or unsubstituted.

A carbocylic ring encompasses 5-membered or 6-membered aromatic or alicyclic ring. Heterocyclic and heteroatomatic rings, as defined herein, are also contemplated.

Preferably, one or both of $R_1$ and $R_2$ and $R_3$ and $R_4$ form together an aromatic ring (including heteroaromatic ring), which can be substituted or unsubstituted. Such moieties are referred to herein as aromatic quinones, and include, for example, benzoquinone, anthraquinone, phenanthrenequinone, each being substituted or unsubstituted, as described herein.

In Scheme 1 above, the moiety on the left (A) represents a moiety featuring atoms in a reduced state (reduced oxidation number) and the moiety on the right (B) represents a moiety featuring atoms in elevated oxidation number, and transformation between the two states is effected by proton transfer and is referred to herein as redox change or redox transformation.

For detecting a redox reactive species, the moiety A on the left in scheme 1 is to be used for generating a functional moiety on the nanostructure surface. Such a moiety, in the presence of an oxidizing agent, undergoes electron delocalization and proton loss, and generates the moiety B on the right in scheme 1.

For detecting a reducing species, the moiety on the right is to be used.

Additional exemplary functional groups that can be included in functional moiety 49 include, but are not limited to, NADH and analogs thereof, as depicted in Schemes 2-4 below; $FADH_2$ and analogs thereof, as depicted in Scheme 5, ferrocene and analogs, derivatives and metal complexes thereof, as depicted in Scheme 6, porphyrinogenic organometallic complexes, ferrocyanide and analogs thereof.

Scheme 2

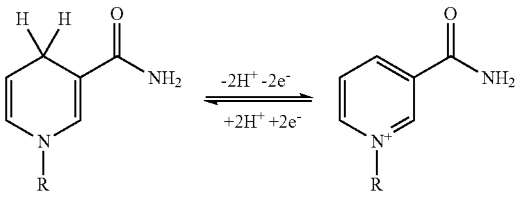

Scheme 3

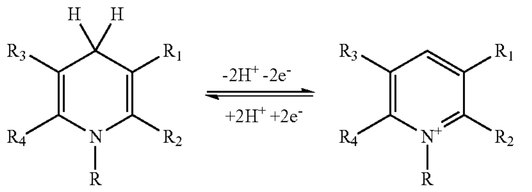

wherein R and $R_1$-$R_4$ are each independently selected from the group consisting of hydrogen, alkyl, aryl, cycloalkyl, halo, trihaloalkyl, alkoxy, carboxy and any other chemically compatible substituent, as described herein, or, alternatively, $R_1$ and $R_2$ and/or $R_3$ and $R_4$ form together a carbocylic ring, which can be substituted or unsubstituted, as defined herein.

Exemplary such functional moieties are depicted in Schemes 4-6 below.

Scheme 4

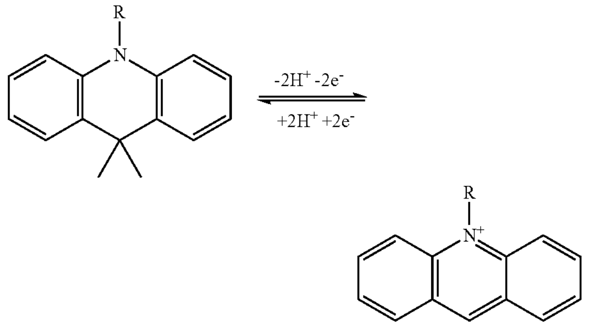

Scheme 5

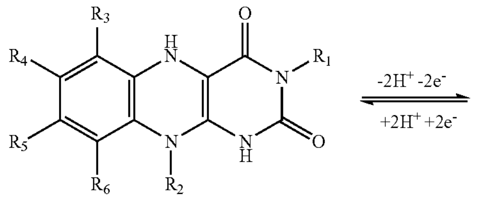

-continued

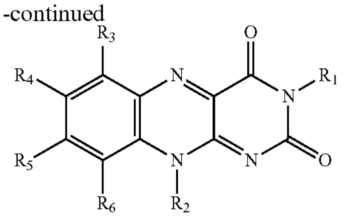

wherein $R_1$-$R_6$ are each independently selected from the group consisting of hydrogen, alkyl, aryl, cycloalkyl, halo, trihaloalkyl, alkoxy, carboxy and any other chemically compatible substituent, as described herein, or, alternatively, two or more of $R_2$-$R_6$ form together a carbocylic ring, which can be substituted or unsubstituted, as defined herein.

Scheme 6

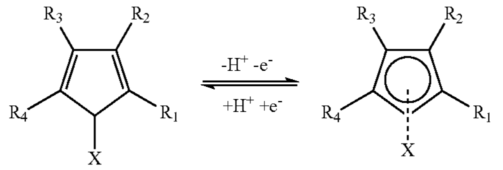

wherein $R_1$-$R_4$ are each independently selected from the group consisting of hydrogen, alkyl, aryl, cycloalkyl, halo, trihaloalkyl, alkoxy, carboxy and any other chemically compatible substituent, as described herein, or, alternatively, two or more of $R_1$-$R_4$ form together a carbocylic ring, which can be substituted or unsubstituted, as defined herein; and X is hydrogen or, preferably a metal atom or ion, optionally further substituted by additional, one or more, ferrocene moiety or moieties, which can be the same or different. It is to be noted that if more than one ferrocene moiety are present, the redox reaction involves electron transfer that corresponds to the number of ferrocene moieties.

Exemplary, non-limiting porphyrinogenic organometallic complexes include, porphyrin, tetramethylpyridilporphyrin [5,10,15,20-tetrakis(1-methyl-4-pyridinio)-porphine] [TMPyP]; tetrahydroxyphenylporphyrine [5,10,15,20-tetrakis(4-hydroxyphenyl)-21H,23H-porphine][TP(OH)P]; tetraphenylporphyrin [5,10,15,20-tetraphenyl-21H,23H-porphine][TPP]; 4,4',4",4"-(porphine-5,10,15,20-tetrayl) tetrakis(benzenesulfonic acid) [TBSP]; hematoporphyrin; protoporphyrin IX, chlorophylle, heme and corrin, complexed with a transition metal such as, for example, cobalt [Co], nickel [Ni], iron [Fe], zinc [Zn], and copper [Cu]. Other metals are and porphyrinogenic ligands and any combination thereof are also contemplated.

According to some of any of the embodiments described herein for a sensing system for detecting redox reactive species, the redox reactive species is an oxidizer and the functional moiety is in its reduced state, such that upon contacting an oxidizer, it is oxidized and as result and generates a change in electrical property of the nanostructure.

In some embodiments, when the functional moiety is oxidized by an oxidizer, the electron density on the nanostructure surface is reduced. When the functional moiety is reduced, electron density on the nanostructure surface is increased.

In some of any of the embodiments described herein, functional moiety 49 is covalently attached to the surface of nanostructure 40 by means of covalent bonds formed between reactive groups within the functional moiety and compatible reactive groups on the surface of the nanostructures, directly or via a linker.

Reactive groups on the nanostructure's surface are either intrinsic or can be generated upon a suitable treatment. In some embodiments, where the nanostructure is a silicon nanowire or a silicon nanotube, free hydroxyl groups are optionally and preferably intrinsically present on the surface of the nanostructures and can be utilized for attaching functional moieties thereto.

Alternatively, the nanostructures described herein are first surface-modified so as to generate surface reactive groups. Such a surface modification can be performed by, for example, attaching to intrinsic functional groups on the nanostructure surface a bifunctional linker molecule, which comprises in one terminus thereof a reactive group that is capable of forming a bond with these intrinsic functional groups and in another terminus thereof a reactive group that can form a bond with the functional moiety as described herein or with a reactive group therein.

In some of any of the embodiments described herein, the functional moiety comprises, prior to being attached to the nanostructure, a reactive group that can readily react with a reactive group on the nanostructure surface, as described herein, so as to form a covalent bond with the nanostructure surface.

Selecting reactive groups that are compatible with functional groups on the nanostructure of choice is within the capabilities of any person skilled in the art, particularly in view of the guidance provided herein.

In some embodiments, when the nanostructure is a silicon nanowire or a silicon nanotube, the functional moiety comprises a reactive group capable of forming covalent bond with free hydroxy groups on the nanostructure surface. Exemplary such reactive groups include, but are not limited to, halides and alkoxides, which can act as leaving groups so as to form an ether bond, carboxylic acids or esters, which can form an ester bond via esterification or trans esterfication, as well as halosilanes and orthosilicates, which can form —Si—O— bonds.

According to some embodiments of the invention, the functional moiety is attached to the nanostructure via any one of the bonds described herein.

In some embodiments, the functional moiety is attached to the nanostructure via a bifunctional linker, as described herein.

An exemplary such a linker is derived from an orthosilicate that comprises 1, 2 or 3 —OR groups attached to Si, for forming —Si—O—Si bonds with intrinsic hydroxyl groups on the silicon nanostructure surface, and 1, 2 or 3 hydrocarbon groups (e.g, alkyl, alkylene, cycloalkyl, aryl) terminating with a reactive group that is capable of reacting with a reactive group of the functional moiety as described herein, such that the total number of groups attached to the Si atom is 4.

In exemplary embodiments, the linker is an orthosilicate comprising an aminoalkyl, one or more alkyl groups and one or more alkoxy groups attached to the Si atom. In one example, the linker is derived from (3-aminoalkyl)-orthosilicatedimethyl-ethoxysilane (APDMES). Such linkers generate a reactive amine group on the surface of the nanostructure. Similar orthosilicate terminating with other reactive groups, such as, for example, described herein, are also contemplated.

The functional moiety can be attached to the nanostructure by means of a reactive group that is compatible with a reactive group on the nanostructure surface. A functional moiety as described herein is optionally and preferably derived from a compound featuring a redox reactivity as described herein, which further comprises a reactive group as described herein, directly or indirectly (e.g., via a linker) attached thereto.

For compounds as presented in Schemes 1, 3, 5 and 6 herein, the reactive group can be, or form a part of (as a substituent), any one or $R_1$-$R_4$ or $R_1$-$R_6$ or, a substituent on the carbocylic ring(s) formed by $R_1$ and $R_2$ and/or $R_3$ and $R_4$, or $R_1$-$R_4$, or $R_2$-$R_6$ as described herein.

For porphyrinogenic complexes, the reactive group can be a substituent of the porphyrin-type ligand.

In an exemplary embodiment, the functional moiety is attached to the nanostructure via a sulfonamide bond, formed from a sulfonate reactive group and an amine reactive group.

In an exemplary embodiment, the functional moiety is a quinone, as described herein, preferably an aromatic quinone, which comprises one or more sulfonate-containing substituents. In an exemplary embodiment, such a functional moiety is attached to modified nanowires exhibiting amine groups by means of a sulfonamide bond.

Functional moieties which are metal-containing complexes, can be covalently attached to the nanostructure, as described hereinabove, or, alternatively or in addition, be absorbed to the nanostructure surface, non-covalently.

Nanostructure 40 is preferably elongated.

As used herein, a "elongated nanostructure" generally refers to a three-dimensional body which is made of a solid substance, and which, at any point along its length, has at least one cross-sectional dimension and, in some embodiments, two orthogonal cross-sectional dimensions less than 1 micron, or less than 500 nanometers, or less than 200 nanometers, or less than 150 nanometers, or less than 100 nanometers, or even less than 70, less than 50 nanometers, less than 20 nanometers, less than 10 nanometers, or less than 5 nanometers. In some embodiments, the cross-sectional dimension can be less than 2 nanometers or 1 nanometer.

In some embodiments, the nanostructure has at least one cross-sectional dimension ranging from 0.5 nanometers to 200 nanometers, or from 1 nm to 100 nm, or from 1 nm to 50 nm.

The length of a nano structure expresses its elongation extent generally perpendicularly to its cross-section. According to some embodiments of the present invention the length of the nanostructure ranges from 10 nm to 50 microns.

The cross-section of the elongated nanostructure may have any arbitrary shape, including, but not limited to, circular, square, rectangular, elliptical and tubular. Regular and irregular shapes are included.

In various exemplary embodiments of the invention the nanostructure is a non-hollow structure, referred to herein as "nanowire".

A "wire" refers to any material having conductivity, namely having an ability to pass charge through itself.

In some embodiments, a nanowire has an average diameter that ranges from 0.5 nanometers to 200 nanometers, or from 1 nm to 100 nm, or from 1 nm to 50 nm.

In some embodiments of the present invention, the nanostructure is shaped as hollow tubes, preferably entirely hollow along their longitudinal axis, referred to herein as "nanotube" or as "nanotubular structure".

The nanotubes can be single-walled nanotubes, multiwalled nanotubes or a combination thereof.

In some embodiments, an average inner diameter of a nanotube ranges from 0.5 nanometers to 200 nanometers, or from 1 nm to 100 nm, or from 1 nm to 50 nm.

In case of multi-walled nanotubes, in some embodiments, an interwall distance can range from 0.5 nanometers to 200 nanometers, or from 1 nm to 100 nm, or from 1 nm to 50 nm.

Figure 1D:
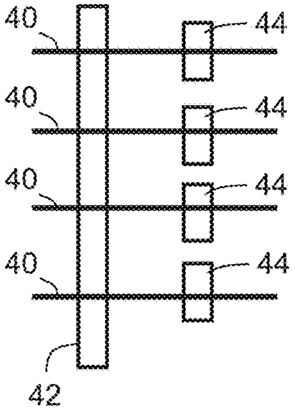

It is appreciated that while FIG. 1C shows a single nanostructure 40, some embodiments contemplate a configuration in which sensing complex 18 comprises a plurality (i.e., two or more) of nanostructure. When a plurality of nanostructures is employed, the nanostructures 40 are optionally and preferably arranged in an array. For example, the nanostructures can be arranged generally parallel to each other, as schematically illustrated in FIG. 1D.

Selection of suitable materials for forming nanostructure 40 as described herein will be apparent and readily reproducible by those of ordinary skill in the art, in view of the guidelines provided herein for beneficially practicing embodiments of the invention. For example, nanostructure 40 of the present embodiments can be made of an elemental semiconductor of Group IV, and various combinations of two or more elements from any of Groups II, III, IV, V and VI of the periodic table of the elements.

As used herein, the term “Group” is given its usual definition as understood by one of ordinary skill in the art. For instance, Group III elements include B, Al, Ga, In and Tl; Group IV elements include C, Si, Ge, Sn and Pb; Group V elements include N, P, As, Sb and Bi; and Group VI elements include O, S, Se, Te and Po.

In some embodiments of the present invention the nanostructure is made of a semiconductor material, optionally and preferably a semiconductor material that is doped with donor atoms, known as “dopant”. The present embodiments contemplate doping to effect both n-type (an excess of electrons than what completes a lattice structure lattice structure) and p-type (a deficit of electrons than what completes a lattice structure) doping. The extra electrons in the n-type material or the holes (deficit of electrons) left in the p-type material serve as negative and positive charge carriers, respectively. Donor atoms suitable as p-type dopants and as n-type dopants are known in the art.

For example, the nanostructure can be made from silicon doped with, e.g., B (typically, but not necessarily Diborane), Ga or Al, to provide a p-type semiconductor nanostructure, or with P (typically, but not necessarily Phosphine), As or Sb or to provide an n-type semiconductor nanostructure.

In experiments performed by the present inventors, Si nanowires and p-type Si nanowires with a diborane dopant have been utilized.

In some embodiments of the present invention the nanostructure is made of, or comprises, a conductive material, e.g., carbon. For example, the nanostructure can be a carbon nanotube, either single-walled nanotubes (SWNT), which are can be considered as long wrapped graphene sheets, or multi walled nanotubes (MWNT) which can be considered as a collection of concentric SWNTs with different diameters. A typical diameter of a SWNT is less of the order of a few nanometers and a typical diameter of a MWNT is of the order of a few tens to several hundreds of nanometers.

When a plurality of nanostructures is employed, the nanostructures can be grown using, for example, chemical vapor deposition. Alternatively, the nanostructures can be made using laser assisted catalytic growth (LCG). Any method for forming a semiconductor nanostructure and of constructing an array of a plurality of nanostructures is contemplated. When a plurality of nanostructures 40 is employed, there is an affinity moiety 48 immobilized on each of the nanostructures. In some embodiments of the present invention all the affinity moieties are the same across all the nanostructures, and in some embodiments at least two nanostructures are attached to different affinity moieties. In some embodiments of the present invention only one type of affinity moiety 48 is included in each microneedle 16, but at least two of microneedles 16 include a nanostructure with different affinity moieties. Use of two or more affinity moieties on respective two or more nanostructures is advantageous since it allows system 10 to sense more than one type of target molecule, sequentially or simultaneously.

A reaction event between reaction product 51 and moiety 49 changes the surface potential of nanostructure 40 and therefore results in a change of an electrical property of nanostructure 40. For example, nanostructure 40 can exhibit a change in density of electrons or holes over some region of nanostructure 40 or over the entire length of nanostructure 40. Nanostructure 40 can additionally or alternatively exhibit a change in its conductivity or resistivity.

The change electrical property of nanostructure 40 can be monitored according to some embodiments of the present invention by an arrangement of electrodes, thereby allowing an indirect monitoring the presence, absence or level of bioanalyte 50 in skin 30, via the reaction of product 51 with moiety 49. In some embodiments of the present invention sensing complex 18 comprises a source electrode 42 and a drain electrode 44, wherein nanostructure 40 is disposed between electrodes 42 and 44 and serves as a charge carrier channel. Optionally, sensing complex 18 also comprises a gate electrode 46, forming, together with electrodes 42 and 44 and nanostructure 40, a transistor, e.g., a field effect transistor (FET). The gate electrode 46 is optionally and preferably, but not necessarily, spaced apart from nanostructure 40 by a gap 47. A gate voltage can be applied to channel nanostructure 40 through gate electrode 46. In some embodiments, when the voltage of gate electrode 46 is zero, nanostructure 40 does not contain any free charge carriers and is essentially an insulator. As the gate voltage is increased, the electric field caused attracts electrons (or more generally, charge carriers) from source electrode 42 and drain electrode 44, and nanostructure 40 becomes conducting. In some embodiments, no gate voltage is applied and the change in the charge carrier density is effected solely by virtue of the interaction between affinity moiety 48 and bioanalyte 50.

It is appreciated that when the electrical property of the nanostructure varies in response to the binding between the affinity moiety and the bioanalyte, a detectable signal can be produced. For example, a change in the electrical property of the channel induces a change in the characteristic response of the transistor to the gate voltage (e.g., the source-drain current as a function of the time for a fixed gate voltage, or a fixed source-drain voltage), which change can be detected and analyzed.

It was found by the present inventors that a gate voltage that is applied to the gate electrode can be used for reversing the redox transformation exhibited by the functional moiety on the surface of the nanostructure. It was also found by the present inventors that gate voltage can be used to control the amount of moieties that can be oxidized on the surface of the nanostructure. Thus, in some embodiments of the present invention the gate voltage that is applied to the gate electrode is selected to maintain a generally constant, and optionally and preferably predetermined, population of the functional moiety on the surface of the nanostructure. Preferably the gate voltage is constant. Once the nanostructure is contacted with an oxidizing agent (e.g., ROS, $H_2O_2$) the equilibrium condition achieved by the gate voltage is changed, since the presence of the oxidizing agent reduces the population level of the functional moiety. This reduction changes the electrical property (e.g., conductivity) of the nanostructure.

The electrodes of sensing complex 18 are optionally and preferably connected by electrical conductors 52 directly or indirectly to circuit 20. In the representative illustration of FIG. 1A, which is not to be considered as limiting, an adapter circuit 54 is used, wherein electrical conductors 52 are connected to adapter circuit 54 and adapter circuit 54 is connected to circuit 20. Circuit 20 applies voltage to nanostructure 40 via one or more of the electrodes, and monitors the changes in the electrical property of nanostructure 40 responsively to the binding of bioanalyte 50 to affinity moiety 48. Circuit 20 can be constructed, for example, for measuring an electrical measure corresponding to a change in the electrical property of nanostructure(s) 40. The electrical measure can be, e.g., voltage, current, conductivity, resistance, impedance, inductance, charge, etc. Circuit 20 typically includes a power source and a voltmeter or amperemeter. In some embodiments a conductance change of less than 10,000 nS can be detected, in some embodiments a conductance change of less than 1,000 nS can be detected, in some embodiments a conductance change of less than 100 nS can be detected, in some embodiments a conductance change of less than 10 nS can be detected, and in some embodiments a conductance change of less than 1 nS can be detected.

When the reaction between reaction product 51 and functional moiety 49 is a redox reaction (e.g., when reaction product 51 comprises a redox reactive species as described herein), circuit 20 is optionally and preferably configured for controlling the gate voltage such as to reverse the redox reaction, as further detailed hereinabove.

In some embodiments of the present invention system 10 comprises one or more calibration microneedles 17, which are also outwardly protruding from the skin contact surface, similarly to sensing microneedles 16. Calibration microneedle(s) 17 optionally and preferably has therein a calibration complex 21 which comprises a calibration nanostructure. The calibration nanostructure is not specifically shown but is generally the same as nanostructure 40, and is preferably also modified by functional moiety 48 and is operationally associated with electrodes such as, but not limited to, electrodes 42, 44 and 46 as further detailed hereinabove. Unlike sensing complex 18, calibration complex 21 is preferably devoid of the affinity moiety 49. For example, sensing complex 18 can be devoid of any affinity moiety, or include a moiety having affinity to a substance other than bioanalyte 50 but have a sufficiently low affinity to bioanalyte 50 (e.g., a binding affinity that is about 10-fold or about 100-fold or about 1000-fold less than the binding affinity of affinity moiety 48 bioanalyte 50), or include a non-sensing moiety.

Calibration microneedle 17 can optionally and preferably be utilized for self-calibration of system 10. In these embodiments, circuit 20 optionally and preferably applies voltage to the calibration nanostructure and subtract changes in an electrical property of the calibration nanostructure from the changes in the electrical property of the nanostructure 40 that is sensing microneedle 16. Since calibration complex 21 is devoid of any moiety that specifically binds to bioanalyte 50, no interaction that is specific to bioanalyte 50 occurs within calibration microneedle 17, so that a signal detected from the calibration represents a background of the physiological environment in skin 30.

In some embodiments of the present invention system 10 comprises a drug delivery system 60 having one or more actuators 62, attached to or integral with substrate 12, and a controller 64. In the representative illustration of FIG. 1A, which is not to be considered as limiting, actuator 62 is attached to or is integral with fluidic interface 56, and controller is at an opposite side of substrate 12 relative to microneedle(s) 16. Controller 64 receives from circuit 20 a signal pertaining to the binding between moiety 48 and bioanalyte 50, and operates actuator 62 to deliver a drug via one or more drug delivery channels responsively to the signal. The drug is optionally and preferably other than the affinity moiety of sensing complex 18 and other than bioanalyte 50. The channel drug delivery can be in the same microneedle 16 as sensing complex 18, or, as illustrated in FIG. 1A, in an additional microneedle 66, outwardly protruding from substrate 12. Similarly to microneedle 16, microneedle 66 also includes one or more openings (not shown) for allowing the drug to exit the microneedle 66.

As used herein, a "drug" is defined as any therapeutically, prophylactically and/or pharmacologically or physiologically beneficial active substance, or mixture thereof, which is delivered to a living organism to produce a desired, usually beneficial, effect. More specifically, any drug which is capable of producing a pharmacological response, localized or systemic, irrespective of whether therapeutic, diagnostic, or prophylactic in nature, is contemplated. The drug may be pharmacologically active or may require further biotransformation. The term "drug" encompasses both "parent drug" and "prodrug" as defined below. The amount of drug that is delivered is sufficient to prevent, cure, diagnose or treat a disease or other condition.

As used herein, a "parent drug" is defined the same as a "drug," except that it does not undergo biotransformation to render it more pharmacologically active.

As used herein, a "prodrug" is defined as a pharmacologically less active derivative of a parent drug molecule that requires biotransformation, either spontaneous or enzymatic, within the organism to release the more active parent drug. Prodrugs are variations or derivatives of the parent drugs which have groups cleavable under metabolic conditions. Prodrugs become the parent drugs which are pharmaceutically active in vivo, when they undergo solvolysis under physiological conditions or undergo enzymatic degradation. Prodrugs may be called single, double, triple, etc., depending on the number of biotransformation steps required to release the active parent drug within the organism, and indicating the number of functionalities present in a precursor-type form. Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative.

The amount of active substance distributed by system 60 can vary from picogram levels to milligram levels, depending on the size of the channel and/or encapsulation efficiency. Non-limiting examples of active substances include organic materials such as horseradish peroxidase, phenolsulfonphthalein, nucleotides, nucleic acids (e.g., oligonucleotides, polynucleotides, siRNA, shRNA), aptamers, antibodies or portions thereof (e.g., antibody-like molecules), hormones (e.g., insulin, testosterone), growth factors, enzymes (e.g., peroxidase, lipase, amylase, organophosphate dehydrogenase, ligases, restriction endonucleases, ribonucleases, RNA or DNA polymerases, glucose oxidase, lactase), cells (e.g., red blood cells, stem cells), bacteria or viruses, other proteins or peptides, small molecules (e.g., dyes, amino acids, vitamins, antioxidants), lipids, carbohydrates, chromophores, light emitting organic compounds (such as luciferin, carotenes) and light emitting inorganic compounds (e.g., chemical dyes and/or contrast enhancing agents such as indocyanine green), immunogenic substances such as vaccines, antibiotics, antifungal agents, antiviral agents, therapeutic agents, diagnostic agents or pro-drugs, analogs or combinations of any of the foregoing.

When there is more than one drug delivering channel, system 60 can deliver two or more drugs, from two or more respective drug delivering channels. Alternatively, all the drug delivering channels can deliver the same drug.

The drug(s) is optionally and preferably contained in one or more drug reservoirs 68 which is in fluid communication, directly or via a fluidic channel (not shown), with microneedle 66, such that the drug can flow from reservoir 68, through the microchannel in microneedle 66 tip, into the skin 30. Reservoir 68 can be part of fluidic interface 56, as illustrated in FIG. 1A. For example, reservoir 68 can be integral with interface 56 to form a monolithic fluidic interface. Alternatively, reservoir 68 can be at the opposite side of substrate 12 relative to microneedle(s) 66. Reservoir 68 can be substantially rigid or readily deformable. Reservoir 68 can be formed from one or more polymers, metals, ceramics, or combinations thereof. In some embodiments, the reservoir includes a volume surrounded by one or more walls, or includes a porous material, such as a sponge, which can retain, for example, the drug until the material is compressed. In some embodiments, the reservoir is formed of an elastic material, such as an elastomeric polymer or rubber. For example, the reservoir can be a balloon-like pouch that is stretched (in tension) when filled with a fluid drug composition to be delivered.

Actuator 62 can be any type of microfluidic actuator that can force drug liquid through the drug delivery microneedle(s). While FIG. 1A illustrates only one actuator for clarity of presentation, system 10 can include more than one actuator, for example, one actuator for each microneedle. In some embodiments, the same actuator can be used for forcing drug liquid through more than one microneedle. Actuator 62 can be mechanical actuator or non-mechanical. When actuator 62 is a mechanical microfluidic actuator, it can include a moving surface, e.g., a diaphragm, that pressurizes a volume of the drug through the drug delivery channel. When actuator 62 is a non-mechanical microfluidic actuator, electrical, magnetic, optical, chemical, or electrochemical energy is used to pressurize a volume of a volume of the drug through the drug delivery channel. For example, actuator 62 can be a phase-change microfluidic actuator that uses heat or electrochemical effects to convert a liquid phase to a gas phase, wherein the pressure associated with the phase change forces the drug through the drug delivery channel. actuator 62 can alternatively be an electroosmotic microfluidic actuator that use body forces on mobile ions in the fluid phase of an electric double layer at a fluid-solid interface to pressurize the drug through the drug delivery channel.

Controller 64 optionally and preferably includes or is associated with a data processor (not shown), which is preferably a dedicated circuit. Controller 64 preferably operates actuator 62 automatically based on signals received from circuit 20 and according to a predetermined drug delivery protocol. Controller 64 and circuit 20 optionally and preferably form a closed-loop system that does not requiring user inputs for either sensing the level of the bioanalyte 50 and for operating the actuator 62 to deliver the drug. For example, controller 64 can be configured for delivering the drug whenever the level of bioanalyte 50 is below and/or above a predetermined threshold. The threshold can be global or, more preferably, subject specific, in which case the threshold can be adjusted. For example, controller 64 can be provided with a data connector 70 through which the threshold or other types of data can be communicated into and/or out of controller 64.

In some embodiments, controller 64 can estimate the level of a substance in the blood of the subject based on the signal received from circuitry 20. This is particularly useful, for example, when bioanalyte 50 is a glucose molecule. It is recognized that glucose levels in interstitial fluid temporally lag behind blood glucose values (typically about five minutes behind), which lag can create issues during times of rapidly changing glucose levels. In the present embodiment, controller 64, via its data processing capabilities, determines an estimated blood glucose level based on the subcutaneous glucose level measured by sensing complex 18. For example, an algorithm can be applied to the glucose levels as sensed by sensing complex 18 to arrive at the blood glucose levels of the subject. The algorithm can transform the sensed interstitial fluid glucose levels to the concentration or levels of glucose, and adjust for time lag between interstitial fluid levels and blood glucose levels. Based on the calculated blood glucose levels and time lag, controller 64 can operate actuator 62 to ensure that the blood glucose levels of the subject are within a predetermine blood glucose level range.

In some embodiments of the present invention system 10 comprises a protective coating 72 encapsulating circuit 20 and/or controller 64. Protective coating 72 can be for example, a waterproof coating of the like.

It is expected that during the life of a patent maturing from this application many relevant nanostructures, affinity moieties and methods of producing same will be developed and the scope of these terms is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find support in the following examples.

EXAMPLES

Reference is now made to the following examples, which together with the above descriptions illustrate some embodiments of the invention in a non limiting fashion.

Example 1

Experimental

Materials and Methods

An array of Silicon Nanowire (SiNW) FETs, each about 20 nm in diameter, was fabricated by photolithography. After deposition of SiNW on a silicon substrate, source and drain electrodes of FETs were defined with a multilayer photoresist structure consisting of LOR5A (Microchem) and S1805 (Shipley). The gap between the source and drain electrodes of the FETs was 2 μm. After exposure and development of the photoresists, the patterns were metallized by e-beam evaporation of Ti/Pd/Ti (5/60/10 nm, respectively). Electrodes were thereafter insulated with a layer of 60 nm $Si_3N_4$, deposited by plasma-enhanced chemical vapor deposition at 80° C. (ICP-PECVD, Axic Inc.), and a layer of 20 nm alumina made by atomic layer deposition (ALD) (Savannah 200 system, Cambridge Nanotech).

After fabrication of the SiNW-FET array, the silicon nanowires of the array were chemically modified to perform sensing of metabolites, by immobilizing redox-reversible system. The 9,10-dihydroxyanthracene/9,10-anthraquinone redox-reversible system was selected as the sensing moiety on the SiNW FET arrays, due to the rapid oxidation of the 9,10-dihydroxyanthracene in the presence of metabolic products such as $H_2O_2$ and reactive oxygen species, via conversion to 9,10-anthraquinone. On the other hand, 9,10-anthraquinone in aqueous solution can be reversibly reduced to 9,10-dihydroxyanthracene in the presence of reductants such as N,N-diethylhydroxylamine, or by applying electric potential.

Therefore, in the presence of oxidase enzyme (e.g., glucose oxidase), on or near the nanowire's surface, this modification allows to perform detection of variety of metabolites (like glucose) follows enzymatic reaction which produces $H_2O_2$.

A simulated interstitial fluid was prepared. The fluid included about 25% serum, about 75% phosphate buffered saline (PBS), and various amounts of glucose.

The modified FET of the present example was placed in a channel containing a simulated interstitial fluid. The fluid included about 25% serum, about 75% PBS, and continuously changing amounts of glucose. A data acquisition system was used to measure the drain-source current (IDs) induced during interaction of the FET with the simulated interstitial fluid. Voltage applied between the drain and the source ($V_{SD}$) was 0.3 V, and the voltage applied to the gate (Vg) was −0.5 V. Current-versus-time signals were recorded at 1-second intervals. At the beginning of the measurement 10 mM glucose introduced to the device (at 5 μl/min flow rate) which continuously diluted to 5 mM. At 3500 sec the concentration is raised up again to 10 mM glucose and introduced to the device (at 3 μl/min flow rate).

Results

Figure 2:
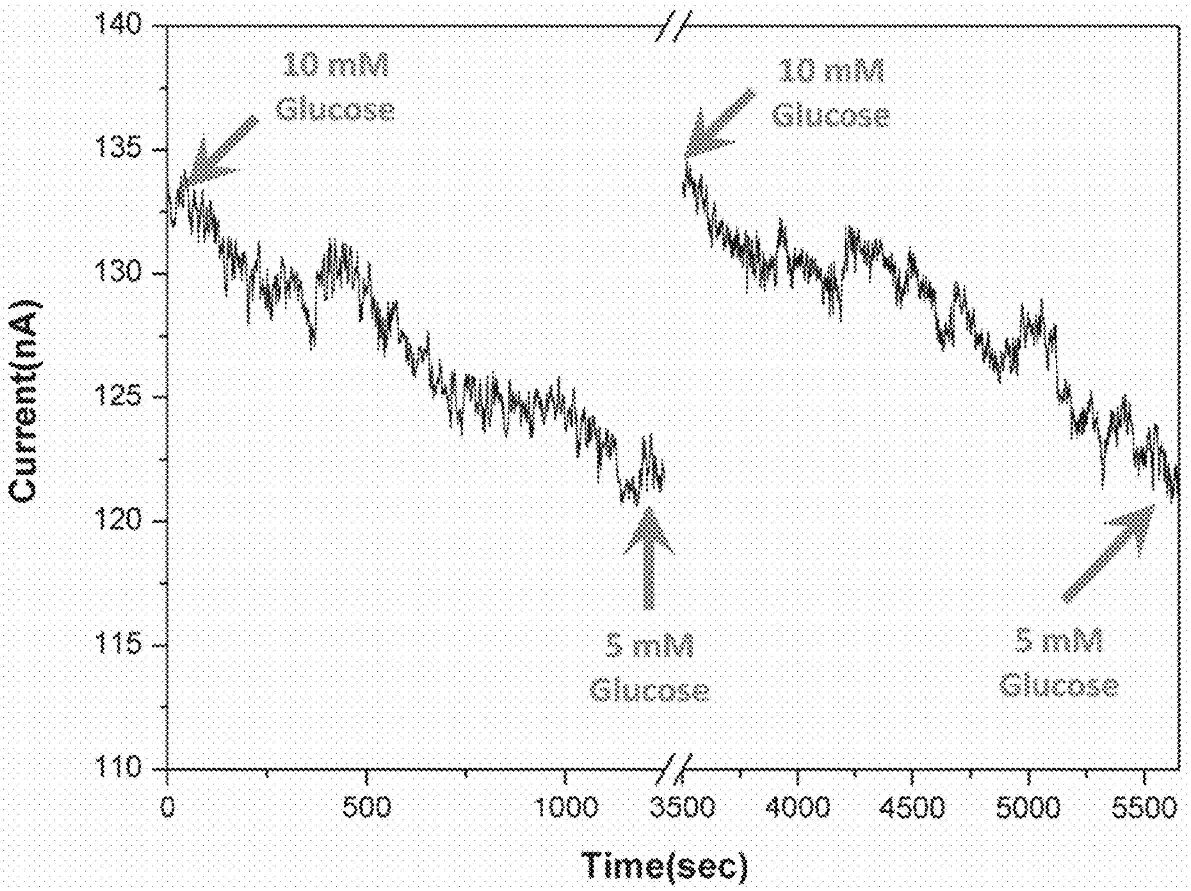
FIG. 2 shows results of continuous glucose monitoring by a FET as obtained in experiments performed according to some embodiments of the present invention.

FIG. 2 shows results of continuous glucose monitoring by the FET of the present Example. Shown is the measured source-drain current in nA as a function of the time. Marked by arrows on the FIG. 2 are time points for glucose concentrations 10 mM and 5 mM in the channel, and a time point at which the fresh fluid was introduced ("tubing change").

As shown, the FET of the present example successfully correlates between the drain-source current and the glucose concentration, with a change of about 15 nA per 5 mM of glucose.

Example 2

A Sensing Element with a Hydrogel

According to some embodiments of the present invention, affinity moiety 48 is immobilized by means of a hydrogel.

In some of these embodiments, the system as described herein further comprises a hydrogel having associated therewith an affinity moiety as described herein.

By "associated with" it is meant that the hydrogel and the affinity moiety are at least in physical interaction, such that the affinity moiety is incorporated in and/or on the hydrogel. The affinity moiety can be absorbed to the surface of the hydrogel, or, preferably, the affinity moiety is entrapped (impregnated) in the hydrogel.

Herein and in the art, the term "hydrogel" describes a three-dimensional fibrous network containing at least 20%, typically at least 50%, or at least 80%, and up to about 99.99% (by mass) water. A hydrogel can be regarded as a material which is mostly water, yet behaves like a solid or semi-solid due to a three-dimensional crosslinked solid-like network, made of natural and/or synthetic polymeric chains, within the liquid dispersing medium. According to some embodiments of the present invention, a hydrogel may contain polymeric chains of various lengths and chemical compositions, depending on the precursors used for preparing it. The polymeric chains can be made of monomers, oligomers, block-polymeric units, which are inter-connected (crosslinked) by chemical bonds (covalent, hydrogen and ionic/complex/metallic bonds, typically covalent bonds). The network-forming material comprises either small aggregating molecules, particles, or polymers that form extended elongated structures with interconnections (the crosslinks) between the segments. The crosslinks can be in the form of covalent bonds, coordinative, electrostatic, hydrophobic, or dipole-dipole interactions or chain entanglements between the network segments. In the context of the present embodiments, the polymeric chains are preferably hydrophilic in nature.

The hydrogel, according to embodiments of the present invention, can be of biological origin or synthetically prepared.

According to some embodiments of the present invention, the hydrogel is biocompatible, and is such that when a biological moiety is impregnated or accumulated therein, an activity is the biological moiety is maintained, that is, a change in an activity of the biological moiety is no more than 30%, or no more than 20%, or no more than 10%, compared to an activity of the biological moiety in a physiological medium. The biological moiety can be affinity moiety 48 or bioanalyte 50.

Exemplary polymers or co-polymers usable for forming a hydrogel according to the present embodiments include polyacrylates, polymethacrylates, polyacrylamides, polymethacrylamides, polyvinylpyrrolidone and copolymers of any of the foregoing. Other examples include polyethers, polyurethanes, and poly(ethylene glycol), functionalized by cross-linking groups or usable in combination with compatible cross linking agents.

Some specific, non-limiting examples, include: poly(2-vinylpiridine), poly(acrylic acid), poly(methacrylic acid), poly(N-isopropylacrylamide), poly(N,N'-methylenbisacrylamide), poly(N—(N-propyl)acrylamide), poly(methacyclic acid), poly(2-hydroxyacrylamide), poly(ethylene glycol) acrylate, poly(ethylene glycol)methacrylate, and polysaccharides such as dextran, alginate, agarose, and the like, and any co-polymer of the foregoing.

Hydrogel precursors forming such polymeric chains are contemplated, including any combination thereof.

Hydrogels are typically formed of, or are formed in the presence of, di- or tri- or multi-functional monomers, oligomer or polymers, which are collectively referred to as hydrogel precursors or hydrogel-forming agents, having two, three or more polymerizable groups. The presence of more than one polymerizable group renders such precursors crosslinkable, and allow the formation of the three-dimensional network.

Exemplary crosslinkable monomers include, without limitation, the family of di- and triacrylates monomers, which have two or three polymerizable functionalities, one of which can be regarded as a crosslinkable functional group. Exemplary diacrylates monomers include, without limitation, methylene diacrylate, and the family of poly (ethylene glycol)$_n$ dimethacrylate (nEGDMA). Exemplary triacrylates monomers include, without limitation, trimethylolpropane triacrylate, pentaerythritol triacrylate, tris (2-hydroxy ethyl) isocyanurate triacrylate, isocyanuric acid tris(2-acryloyloxyethyl) ester, ethoxylated trimethylolpropane triacrylate, pentaerythrityl triacrylate and glycerol triacrylate, phosphinylidynetris(oxyethylene) triacrylate.

Hydrogels may take a physical form that ranges from soft, brittle and weak to hard, elastic and tough material. Soft hydrogels may be characterized by rheological parameters including elastic and viscoelastic parameters, while hard hydrogels are suitably characterized by tensile strength parameters, elastic, storage and loss moduli, as these terms are known in the art.

The softness/hardness of a hydrogel is governed inter alia by the chemical composition of the polymer chains, the "degree of crosslinking" (number of interconnected links between the chains), the aqueous media content and composition, and temperature.

A hydrogel, according to some embodiments of the present invention, may contain macromolecular polymeric and/or fibrous elements which are not chemically connected to the main crosslinked network but are rather mechanically intertwined therewith and/or immersed therein. Such macromolecular fibrous elements can be woven (as in, for example, a mesh structure), or non-woven, and can, in some embodiments, serve as reinforcing materials of the hydrogel's fibrous network. Non-limiting examples of such macromolecules include polycaprolactone, gelatin, gelatin methacrylate, alginate, alginate methacrylate, chitosan, chitosan methacrylate, glycol chitosan, glycol chitosan methacrylate, hyaluronic acid (HA), HA methacrylate, and other non-crosslinked natural or synthetic polymeric chains and the likes. According to some of any of the embodiment of the present invention, the amount of such non-crosslinked additives is small and typically does not exceed 100 mg in 1 ml of the hydrogel-forming precursor solution.

In some embodiments, the hydrogel is porous and in some embodiments, at least a portion of the pores in the hydrogel are nanopores, having an average volume at the nanoscale range. A porous hydrogel allows diffusion of a bioanalyte and/or a reaction product therein and therefrom.

The hydrogel can be in a form of, for example, a film. Alternatively, it can be in a form of a nanoparticle. Other forms are also contemplated.

The hydrogel associated with the affinity moiety is preferably in proximity with the nanostructure(s), for example, within a micrometric distance therewith, such that a bioanalyte and/or a reaction product present in the hydrogel can become in contact with the nano structures.

In some embodiments, the hydrogel is in contact with the nanostructure. The contact can be a physical contact, for example, a hydrogel in a form of a film or nanoparticles contacts (e.g., is absorbed to) the surface of the nanostructure. The contact can be a chemical contact, such that the hydrogel is covalently attached to a surface of a nanostructure by means of covalent bonds formed between the hydrogel and compatible reactive groups on the surface of the nanostructures, directly or via a linker. In some of these embodiments, the hydrogel is in contact with nanostructures other than the nanostructures featuring a functional moiety as described herein. In these embodiments, both the nanostructure that is in contact with the hydrogel and the nanostructure that features a functional moiety are optionally and preferably within the same microneedle.

Reactive groups on the nanostructure's surface are either intrinsic or can be generated upon a suitable treatment. In some embodiments, where the nanostructure is SiNW or silicon nanotubes, free hydroxyl groups are intrinsically present on the surface of the nanostructures and can be utilized for attaching functional moieties thereto.

Alternatively, the nanostructures are first surface-modified so as to generate surface reactive groups. Such a surface modification can be performed by, for example, attaching to intrinsic functional groups on the nanostructure surface a bifunctional linker molecule, which comprises in one terminus thereof a reactive group that is capable of forming a bond with these intrinsic functional groups and in another terminus thereof a reactive group that can covalently attach to the hydrogel.

In some embodiments, the hydrogel is attached to the nanostructure via a bifunctional linker, as described herein.

An exemplary such a linker is derived from a silyl that comprises 1, 2 or 3-living groups that allows the silyl to interact with intrinsic hydroxyl groups on the silicon nanostructure surface, forming —Si—O—Si bonds, and 1, 2 or 3 hydrocarbon groups (e.g, alkyl, alkylene, cycloalkyl, aryl) terminating with a reactive group that is capable of covalently attaching to the hydrogel.

Alternatively, the linker can be derived from an orthosilicate that comprises 1, 2, or 3 OR' groups, with can interact with intrinsic hydroxyl groups on the silicon nanostructure surface, forming —Si—O—Si bonds, and 1, 2 or 3 hydrocarbon groups (e.g, alkyl, alkylene, cycloalkyl, aryl) terminating with a reactive group that is capable of covalently attaching to the hydrogel.

In exemplary embodiments, the reactive group is a polymerizable group that is chemically compatible with one or more polymerizable groups of at least one hydrogel precursor, such that the linker (linking moiety) forms a part of the hydrogel.

For example, if the hydrogel is made of polyacrylate chains, and is formed of diacrylate and/or tri-acrylate precursors as described herein, a suitable linker is derived from a silyl or orthosilicate that comprises one or more hydrocarbon chains, at least one terminating with an acrylate group. The acrylate group polymerizes/cross-links along with the acrylate groups of the hydrogel precursor, resulting is covalent attachment of the hydrogel to the nanostructure's surface.

In some embodiments, when the linker comprises a hydrocarbon chain, which can be of any length. For example, the hydrocarbon chain can be of 1 to $10^6$, or of 1 to $10^3$, or from 1 to 100, or from 1 to 50, or from 1 to 20, or from 1 to 10, carbon atoms in length, including any intermediate values and subranges therebetween.

In exemplary embodiments, the linker is derived from halosilylalkyl (e.g., trichlorosilylalkyl) comprising an alkyl terminating with an acrylate group.

In exemplary embodiments, the linker is derived from alkoxysilylalkyl (e.g., trialkoxysilylalkyl) comprising an alkyl terminating with an acrylate group.

In some of these embodiments, the alkyl is propyl. Other alkyls, for example, ethyl, butyl, pentyl, and hexyl, and higher alkyls are also contemplated.

In exemplary embodiments, a system as described herein comprises a sensing complex which comprises a nanostructure (or a plurality of nanostructures) modified by a functional moiety and a nanostructure (or a plurality of nanostructures) to which a hydrogel associated with the affinity moiety is attached (chemically or physically, as described herein). When the bioanalyte is a metabolite and the affinity moiety is a redox enzyme, a reaction product is formed by an interaction between the metabolite and the enzyme and contacts the nanostructure modified by the functional moiety, and a change in an electrical property of the nanostructure is effected and detected.

The following describes an exemplary procedure for covalently attaching a hydrogel incorporating GOx to SiNWs, to thereby form a sensing complex in which the affinity moiety is associated with a hydrogel that is covalently attached to a nanostructure, whereby the nanostructure is in proximity to a nanostructure modified by a functional moiety as described herein.

SiNW-FET is fabricated according to Patolsky et al., Nat Protoc. 2006; 1(4):1711-24. 20 nm diameter P-type silicon nanowires (SiNW) FET devices are fabricated by photolithography on 3 inch silicon wafer with 600 nm oxide layer. Briefly, source and drain electrodes are deposited with the use of a multilayer photoresist structure consisting of 500 nm LOR5A (Microchem) and 500 nm 1805 (Shipley). After exposure and development of the electrode patterns, the contacts are metallized by e-beam and thermal evaporation of Ni (60 nm) respectively, and are then passivated with an insulating layer of $Si_3N_4$(60 nm thick) deposited by plasma-enhanced chemical vapor deposition at 80° C. (ICP-PECVD, Axic Inc.) and a layer of 10 nm alumina (ALD deposition using a Cambridge Nanotech Savannah 200 system). The separation between the source and drain electrodes for each FET is 2 μm.

Figure 3A:
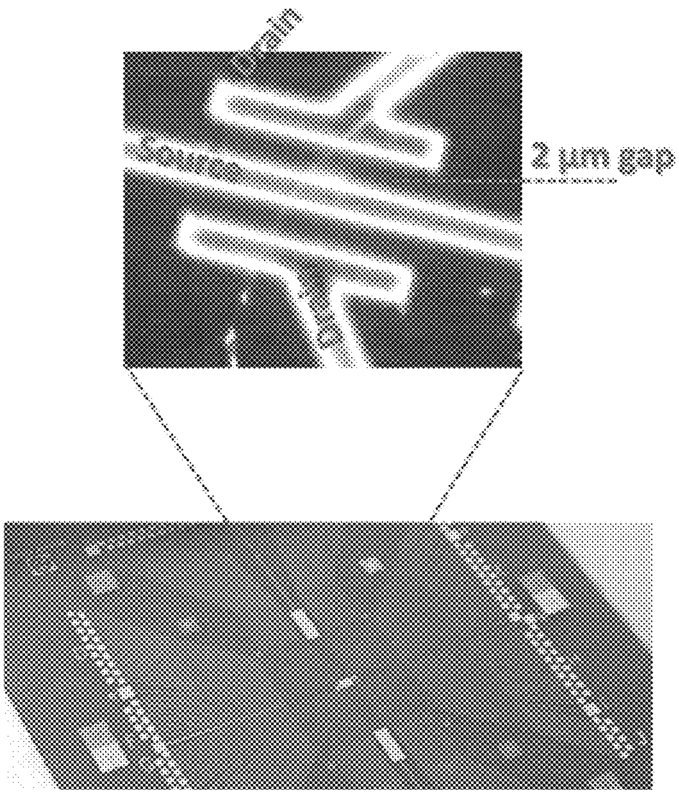
FIG. 3A shows images of a silicon nanowire FET system, fabricated according to some embodiments of the present invention.
Figure 3B:
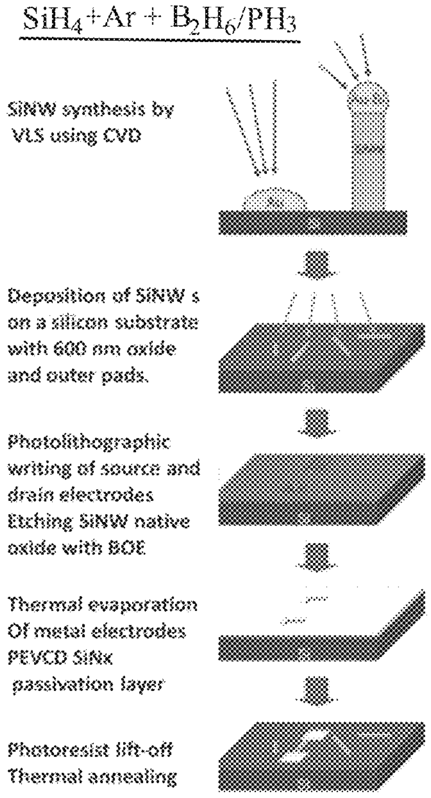
FIG. 3B is a schematic illustration describing a process suitable for fabricating a silicon nanowire FET system, according to some embodiments of the present invention.

The process is schematically illustrated in FIG. 3B, and the SiNW-FET system is schematically illustrated in FIG. 3A.

Figure 4:
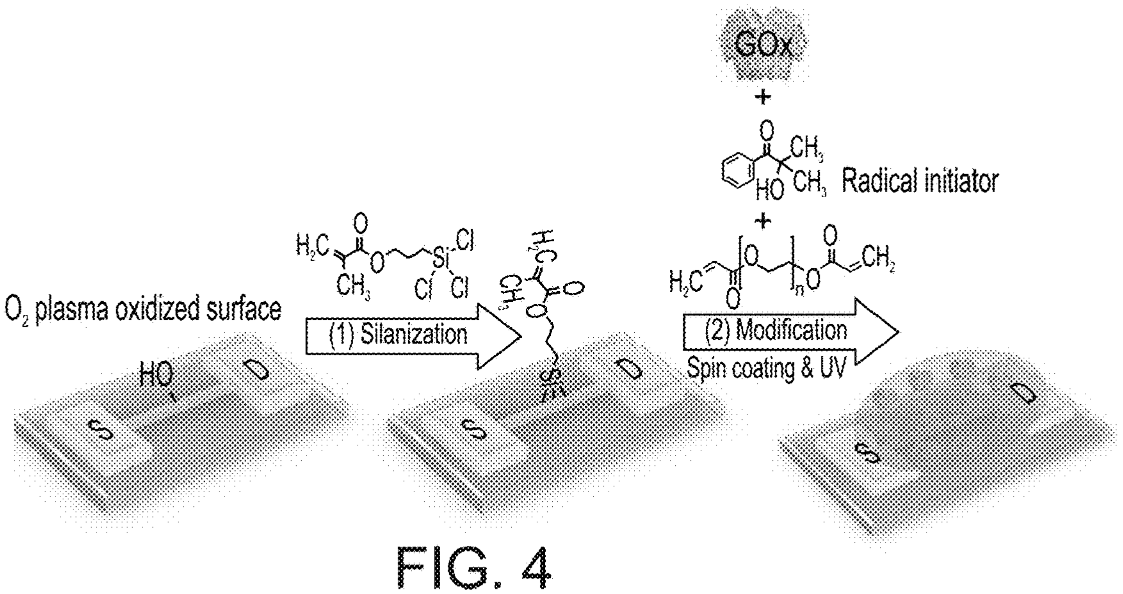
FIG. 4 is a schematic illustration describing a process suitable for modifying of silicon nanowire FET system, according to some embodiments of the present invention.

A modification of SiNW FET system so as to immobilize thereto GOx-impregnated hydrogels is schematically illustrated in FIG. 4, and is briefly described as follow. A SiNW FET prepared as described hereinabove is activated by oxygen plasma treatment (15 minutes, 100 W, 0.400 Torr). The SiNWs are then treated for 60 minutes, at room temperature, with a 1 mM solution of 3-(Trichlorosilyl)propyl methacrylate (TPM) in a mixture of heptane and carbon tetrachloride 4:1 ratio, in a glove box under argon atmosphere, and are thereafter washed with hexane and isopropanol, in accordance with a procedure described in Revzin et al., Langmuir, 2001, 17, 5440-5447. The resulting modified SiNWs feature surface acrylate groups.

Attachment of a hydrogel to the SiNWs surface is performed similar to a procedure described in Piao et al., Biosensors and Bioelectronics 65 (2015) 220-225. A stock solution of poly(ethylene glycol) diacrylate (PEG-DA, MW 575) and 1 wt. % of 2-hydroxy-2-methylpropiophenone (HMPP) initiator is prepared and stored at 4° C. until used. A hydrogel precursor solution comprising of 67 vol. % of PEG-DA stock solution and 3.33 mg/mL glucose oxidase (GOx) in a Tris buffer (pH 7.4) is prepared and deposited on the acrylate-modified SiNW FET by means of spin coating, using spin coater (WS-400B-6NPP/LITE/10K, Laurell Technologies Corporation.), and exposed to UV light (320-380 nm filter), so as to form GOx-impregnating hydrogel film on the surface of the SiNWs. The remaining hydrogel precursor solution is flushed by a phosphate buffered saline (150 mM, pH 7.4).

The resulting modified SiNW FET system features a poly(ethylene glycol)diacrylate hydrogel covalently attached to the SiNWs surface and impregnating GOx therein.

Hydrogels impregnating other affinity moieties are similarly prepared by replacing GOx with a desired affinity moiety and/or using other hydrogel precursor moieties.

Figure 5:
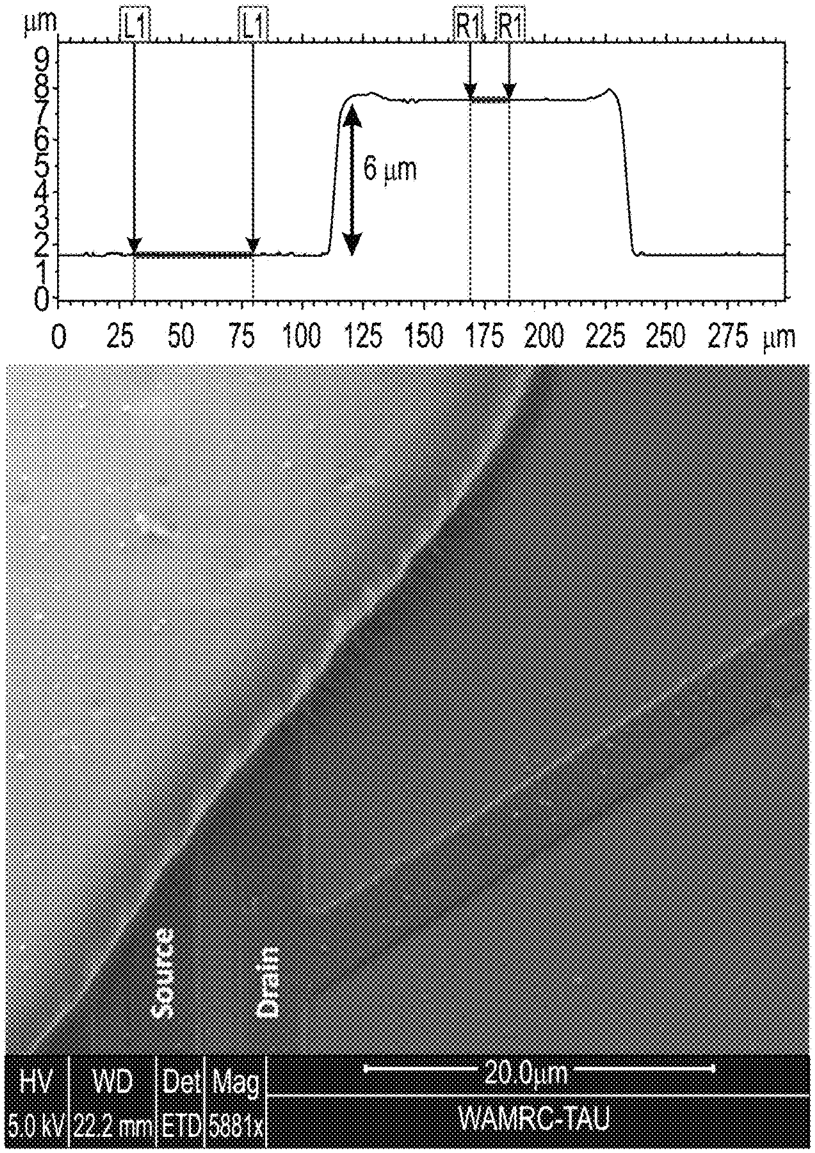
FIG. 5 presents a scanning electron microscope image and a profilometer graph (inset), of source and drain electrodes of a silicon nanowire FET systems device having a GOx-impregnating hydrogel film attached thereto, fabricated according to some embodiments of the present invention.

FIG. 5 presents a scanning electron microscope image, taken using Quanta 200 FEG environmental scanning electron microscope (5 KV, secondary electron imaging), of source and drain electrodes of a silicon nanowire FET system having a GOx-impregnating hydrogel film attached thereto. Shown in the inset are data obtained in profilometer measurements, taken using Profilometer Dektak® 8 Veeco, of the GOx-impregnating hydrogel film on the device, and presenting the thickness of the hydrogel (the height of the hydrogel compared to the silicon wafer surface).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of monitoring at least a presence of a bioanalyte, comprising:

introducing into a skin of a subject, a microneedle having therein a sensing complex comprising a transistor and an affinity moiety effective to react specifically with the bioanalyte to produce a reaction product comprising a redox reactive species, said transistor having a source electrode, a drain electrode, a gate, and a charge carrier channel which is disposed between said source electrode and said drain electrode, wherein the charge carrier channel further comprises a nanostructure modified by a functional moiety covalently attached thereto;

applying a voltage to said nanostructure;

monitoring changes in a source-drain current within said nanostructure responsively to a reaction between said reaction product and said functional moiety of said nanostructure within said microneedle; and applying a gate voltage to said gate to reverse said redox reaction.

2. The method of claim 1, wherein said introducing comprises establishing contact between said skin and a skin contact surface of a substrate, wherein said microneedle outwardly protrudes from said skin contact surface.

3. The method according to claim 1, further comprising delivering a drug through said skin via a drug delivery channel responsively to said monitoring.

4. The method according to claim 3, wherein said drug delivery channel is in said microneedle.

5. The method according to claim 1, further comprising:

introducing into said skin of said subject a calibration microneedle, outwardly protruding from said a skin contact surface, and having therein a calibration complex which comprises a calibration nanostructure modified by said functional moiety covalently attached thereto, but is devoid of said affinity moiety;

applying voltage to said calibration nanostructure; and subtracting changes in a source-drain current of said calibration nanostructure from said changes in the source-drain current of said nanostructure.

6. The method according to claim 1, wherein said functional moiety is a redox reactive moiety.

7. The method according to claim 1, wherein said functional moiety comprises at least one functional group capable of reversible change in an oxidation number or oxidation state of at least one atom of the functional moiety.

8. The method of claim 1, wherein said nanostructure comprises a structure selected from the group consisting of a semiconductor nanostructure, a conductive nanostructure and a carbon nanotube.

9. The method according to claim 1, wherein said affinity moiety is immobilized to said nanostructure.

10. The method according to claim 1, wherein said affinity moiety is immobilized to a medium in said microneedle, other than said nanostructure.

11. The method according to claim 1, wherein said affinity moiety is immobilized to an integral wall of said microneedle.

* * * * *